( 12 ) United States Patent
Daniel et al.

(10) Patent No.: US 6,831,122 B2
(45) Date of Patent: Dec. 14, 2004

(54) WATER-ABSORBING AGENT, METHOD FOR THE PRODUCTION AND THE UTILIZATION THEREOF

(75) Inventors: Thomas Daniel, Waldsee (DE); Ulrich Riegel, Frankfurt (DE); Matthias Weismantel, Jossgrund (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/250,826

(22) PCT Filed: Jan. 18, 2002

(86) PCT No.: PCT/EP02/00484

§ 371 (c)(1),
(2), (4) Date: Nov. 13, 2003

(87) PCT Pub. No.: WO02/060983

PCT Pub. Date: Aug. 8, 2002

(65) Prior Publication Data

US 2004/0077796 A1 Apr. 22, 2004

(30) Foreign Application Priority Data

Jan. 19, 2001 (DE) .......................................... 101 02 429

(51) Int. Cl.⁷ ................................................ C08K 3/32
(52) U.S. Cl. ........................ 524/417; 524/403; 524/556
(58) Field of Search ................................. 524/403, 417, 524/556

(56) References Cited

U.S. PATENT DOCUMENTS

| 4,286,082 A | | 8/1981 | Tsubakimoto et al. |
| 4,732,968 A | * | 3/1988 | Obayashi et al. ........... 528/490 |
| 4,734,478 A | | 3/1988 | Tsubakimoto et al. |
| 5,489,469 A | * | 2/1996 | Kobayashi et al. ......... 442/393 |
| 6,229,062 B1 | * | 5/2001 | Mandell et al. ............. 604/367 |
| 2004/0019342 A1 | * | 1/2004 | Nagasuna et al. |

FOREIGN PATENT DOCUMENTS

| DE | 3523617 | 1/1986 |
| JP | 7-165981 | 6/1995 |
| WO | WO 87/00848 | 2/1987 |
| WO | WO 92/00108 | 1/1992 |
| WO | WO 94/15651 | 7/1994 |
| WO | WO 95/11932 | 5/1995 |

* cited by examiner

Primary Examiner—Helen L. Pezzuto
(74) Attorney, Agent, or Firm—Marshall, Gerstein & Borun LLP

(57) ABSTRACT

Disclosed is a water absorbent comprising particles of a water absorbent polymer whose surface is associated with a water insoluble metal phosphate. It possesses an improved performance profile comprising high absorption capacity, improved fluid transportation performance and a faster swell rate.

25 Claims, No Drawings

WATER-ABSORBING AGENT, METHOD FOR THE PRODUCTION AND THE UTILIZATION THEREOF

The present invention relates to a water absorbent comprising particles of a water absorbent polymer, a process for its production and the use of the water absorbent for absorbing body fluids, for producing hygiene articles and for soil improvement.

Water absorbent polymers, which are also referred to as hydrogel-forming polymers or superabsorbent polymers (hereinafter abbreviated to SAPs), are known. They are networks of flexible hydrophilic polymers, which can be not only ionic but also nonionic in nature. They are capable of absorbing and binding aqueous fluids by forming a hydrogel. A comprehensive survey of SAPs, their use and their manufacture is given in F. L. Buchholz and A. T. Graham (editors) in "Modern Superabsorbent Polymer Technology", Wiley-VCH, New York, 1998.

SAPs are used in particular in hygiene articles such as diapers, incontinence pads and briefs, sanitary napkins and the like to absorb body fluids. A frequent problem is here that the superabsorbent at the point of ingress of the fluid swells to a substantial extent and forms a barrier layer for subsequent amounts of fluid. This prevents any transmission and distribution of the fluid in the absorbent core. This superabsorbent phenomenon is known as gel-blocking. Subsequent amounts of fluid are then no longer absorbed by the absorbent core, with the consequences of uncontrolled distribution of the fluid on the diaper surface and leakage in the extreme case.

DE-A-3 523 617, U.S. Pat. No. 4,734,478 and U.S. Pat. No. 4,286,082 describe water absorbent resins containing silicon dioxide in admixture. The silicon dioxide added is said to reduce the caking tendency of the resin. WO 87/00848 describes the use of colloidal carrier materials, such as colloidal silica, to enhance the gel strength.

WO 95/11932 discloses the addition of finely divided silica to the surface postcrosslinker solution. EP-386 897 discloses the use of polyvalent metal ions as crosslinkers. The polyvalent metals are used in the form of their water soluble salts. However, the performance profile of the water absorbents described is not in every respect satisfactory.

It is an object of the present invention to provide water absorbents possessing improved application properties, especially high absorption capacities under pressure, improved fluid transportation performance and a faster swell rate.

We have found that this object is achieved according to the invention by a water absorbent comprising particles of a water absorbent polymer whose surface is associated with a water insoluble metal phosphate.

The invention further provides a process for producing a water absorbent as claimed in any preceding claim, which comprises
a) intimately mixing a particulate water absorbent polymer with a finely divided water insoluble metal phosphate; or
b) applying a slurry of a finely divided water insoluble metal phosphate to a particulate water absorbent polymer; or
c) contacting a first aqueous solution containing phosphate ions with a second aqueous solution in the presence of a particulate water absorbent polymer, said second solution containing a water soluble salt of a metal forming a water insoluble phosphate.

Conveniently, the water absorbent of the invention generally has a Saline Flow Conductivity (SFC) of at least $30 \times 10^{-7}$ cm$^3$·s/g, an Absorbency Under Load (AUL) (0.7 psi) of at least 20 g/g and a Centrifuge Retention Capacity (CRC) of at least 24 g/g.

The term "associated" is to be understood in the broadest sense and shall comprehend any kind of interaction between the water insoluble metal phosphate and the surface of the particles of the polymer. "Associated" means that the water insoluble metal phosphate is disposed virtually exclusively on the surface of the particles of the water absorbent polymer and only to an insignificant extent, if at all, in the body of the particles. Generally the water insoluble metal phosphate is associated by physical interaction, for example encapsulated in surface irregularities or voids close to the surface.

Useful water insoluble metal phosphates also include phosphates which can be viewed as "phosphates" in the technical sense and can be considered, for example, as mixed phosphate oxides, phosphate hydroxides, phosphate silicates, phosphate fluorides or the like.

Preferred water insoluble metal phosphates are water insoluble metal phosphates which comprise a phosphate of the formula $M_4P_2O_7$, $M_2HPO_4$ or $M_3PO_4$ wherein M is one equivalent of a metal selected from the group consisting of calcium, magnesium, strontium, barium, zinc, iron, aluminum, titanium, zirconium, hafnium, tin, cerium, scandium, yttrium and lanthanum or mixtures thereof. M can also comprise alkali metal phosphates, as long as the mixed phosphate is water insoluble.

Preferred phosphates are calcium hydrogenphosphate, tertiary calcium phosphate, apatite, Thomas flour of the formula $Ca_5(PO_4)[SiO_4]$, berlinite of the formula $AlPO_4$, rhenania phosphate of the formula $3CaNaPO_4.VCa_2SiO_4$. Particular preference is given to tertiary calcium phosphate, calcium hydrogenphosphate and apatite. The term "apatite" comprehends fluoroapatite, hydroxyl apatite, chloroapatite, carbonate apatite and carbonate fluoroapatite. It will be appreciated that mixtures of various water insoluble metal phosphates can be used as well.

When the water absorbent is to be used in a hygiene article, especially physiologically safe water insoluble metal phosphates and mixtures thereof come into consideration, such as tertiary calcium phosphate, hydroxyl apatite or calcium hydrogenphosphate.

The fraction of the water insoluble metal phosphate is customarily in the range of about 0.001–10% by weight, preferably from 0.01 to 5% by weight and very particularly preferably from 0.05 to 2.5% by weight, based on the weight of the water absorbent polymer.

Useful water absorbent polymers are in particular polymers of hydrophilic monomers, graft copolymers of one or more hydrophilic monomers on a suitable grafting base, crosslinked cellulose or starch ethers, crosslinked carboxymethylcellulose, partially crosslinked polyethers or natural products that are swellable in aqueous fluids, such as guar derivatives, alginates and carrageenans.

Suitable grafting bases may be of natural or synthetic origin. They include starches, i.e., native starches from the group consisting of corn (maize) starch, potato starch, wheat starch, rice starch, tapioca starch, sorghum starch, manioca starch, pea starch or mixtures thereof, modified starches, starch degradation products, for example oxidatively, enzymatically or hydrolytically degraded starches, dextrins, for example roast dextrins, and also lower oligo- and polysaccharides, for example cyclodextrins having from 4 to 8 ring members. Useful oligo- and polysaccharides further include cellulose and starch and cellulose derivatives. It is also possible to use polyvinyl alcohols, polyamines, polyamides, hydrophilic polyester or polyalkylene oxides, especially polyethylene oxide and polypropylene oxide. Useful polyalkylene oxides have the general formula I:

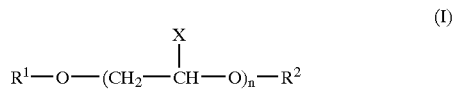

where
R$^1$, R$^2$ are independently hydrogen; C$_1$-C$_4$-alkyl; C$_2$-C$_6$-alkenyl; aryl, especially phenyl; or (meth)acryloyl;
X is hydrogen or methyl, and
n is an integer from 1 to 1000, especially from 10 to 400.

Polymers of monoethylenically unsaturated acids are preferred as water absorbent polymers. Polymers of monoethylenically unsaturated acids are preferably at least partly present in the form of their salts, especially their alkali metal salts, such as sodium or potassium salts, or as ammonium salts. Polymers of this kind are particularly good at gelling on contact with aqueous fluids.

Particular preference is given to crosslinked water absorbent polymers of monoethylenically unsaturated C$_3$-C$_6$-carboxylic acids and/or their alkali metal or ammonium salts. Preference is given in particular to crosslinked polyacrylic acids where from 25 to 100% of the acid groups are present as alkali metal or ammonium salts.

Polymers of this kind are obtained for example on polymerizing monoethylenically unsaturated acids or salts thereof in the presence of crosslinkers. However, it is also possible to polymerize without crosslinker and to crosslink subsequently.

Water absorbent polymers are preferably polymerized from
  from 49.9 to 99.9% by weight of at least one monomer A selected from the group consisting of monoethylenically unsaturated acids and salts thereof,
  from 0 to 50% by weight, preferably from 0 to 20% by weight, of at least one noncrosslinking monoethylenically unsaturated monomer B other than said monomer A, and
  from 0.001 to 20% by weight, preferably from 0.01 to 14% by weight, of at least one crosslinking monomer C.

Useful monomers A include monoethylenically unsaturated mono- and dicarboxylic acids of 3 to 25, preferably 3 to 6, carbon atoms which may also be used as salts or as anhydrides. Examples are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. Useful monomers A further include the monoesters of monoethylenically unsaturated dicarboxylic acids of 4 to 10, preferably 4 to 6, carbon atoms, for example of maleic acid, such as monomethyl maleate. Useful monomers A also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloyloxypropylsulfonic acid, 2-hydroxy-3-methacryloyloxypropylsulfonic acid, styrenesulfonic acid, 2-acrylamido-2-methylpropanesulfonic acid, vinylphosphonic acid and allylphosphonic acid, and the salts, especially the sodium, potassium and ammonium salts, of these acids. The A monomers may be used as such or as mixtures of different A monomers. The weight fractions specified are all based on the acid form.

Preferred A monomers are acrylic acid, methacrylic acid, vinylsulfonic acid, 2-acrylamido-2-methylpropanesulfonic acid or mixtures thereof. Preferred A monomers are acrylic acid and mixtures of acrylic acid with other A monomers, for example mixtures of acrylic acid and methacrylic acid, mixtures of acrylic acid and acrylamidopropanesulfonic acid or mixtures of acrylic acid and vinylsulfonic acid. Acrylic acid is particularly preferably the main constituent of the A monomers.

To optimize properties of the polymers according to the invention, it can be sensible to use additional monoethylenically unsaturated monomers B that differ from the A monomers in that they bear no acid groups, but are copolymerizable with the A monomers and are noncrosslinking. Such compounds include for example monoethylenically unsaturated nitriles such as acrylonitrile, methacrylonitrile, the amides of the aforementioned monoethylenically unsaturated carboxylic acids, e.g., acrylamide, methacrylamide, N-vinylamides such as N-vinylformamide, N-vinylacetamide, N-methylvinylacetamide, N-vinylpyrrolidone and N-vinylcaprolactam. The monomers also include vinyl esters of saturated C$_1$-C$_4$-carboxylic acids such as vinyl formate, vinyl acetate and vinyl propionate, alkyl vinyl ethers having at least 2 carbon atoms in the alkyl group, e.g., ethyl vinyl ether or butyl vinyl ether, esters of monoethylenically unsaturated C$_3$-C$_6$-carboxylic acids, for example esters of monohydric C$_1$-C$_{18}$-alcohols and acrylic acid, methacrylic acid or maleic acid, acrylic and methacrylic esters of alkoxylated monohydric saturated alcohols, for example of alcohols having 10 to 25 carbon atoms which have been reacted with from 2 to 200 mol of ethylene oxide and/or propylene oxide per mole of alcohol, and also monoacrylates and monomethacrylates of polyethylene glycol or polypropylene glycol, the molar masses (M$_n$) of the polyalkylene glycols being up to 2 000, for example. Further suitable monomers are styrene and alkyl-substituted styrenes such as ethylstyrene or tert-butylstyrene.

The B monomers may also be used as mixtures of different B monomers, for example mixtures of vinyl acetate and 2-hydroxyethyl acrylate in any ratio.

Useful crosslinking C monomers include compounds having at least two, for example 2, 3, 4 or 5, ethylenically unsaturated double bonds in the molecule. Examples of compounds of this type are N,N'-methylenebis-acrylamide, polyethylene glycol diacrylates and polyethylene glycol dimethacrylates each derived from polyethylene glycols having a molecular weight of from 106 to 8 500, preferably from 400 to 2 000, trimethylolpropane triacrylate, trimethylolpropane trimethacrylate, ethylene glycol diacrylate, ethylene glycol dimethacrylate, propylene glycol diacrylate, propylene glycol dimethacrylate, butanediol diacrylate, butanediol dimethacrylate, hexanediol diacrylate, hexanediol dimethacrylate, diethylene glycol diacrylate, diethylene glycol dimethacrylate, triethylene glycol diacrylate, triethylene glycol dimethacrylate, dipropylene glycol diacrylate, dipropylene glycol dimethacrylate, tripropylene glycol diacrylate, tripropylene glycol dimethacrylate, allyl methacrylate, diacrylates and dimethacrylates of block copolymers of ethylene oxide and propylene oxide, di-, tri-, tetra- or pentaacrylated or -methacrylated polyhydric alcohols, such as glycerol, trimethylolpropane, pentaerythritol or dipentaerythritol, esters of monoethylenically unsaturated carboxylic acids with ethylenically unsaturated alcohols such as allyl alcohol, cyclohexenol and dicyclopentenyl alcohol, e.g., allyl acrylate and allyl methacrylate, also triallylamine, dialkyldiallylammonium halides such as dimethyldiallylammonium chloride and diethyldiallylammonium chloride, tetraallylethylenediamine, divinylbenzene, diallyl phthalate, polyethylene glycol divinyl ethers of polyethylene glycols having a molecular weight of from 106 to 4 000, trimethylolpropane diallyl ether, butanediol divinyl ether, pentaerythritol triallyl ether, reaction products of 1 mol of ethylene glycol diglycidyl ether or polyethylene glycol diglycidyl ethers with 2 mol of pentaerythritol triallyl ether or allyl alcohol, and divinylethyleneurea.

Preference is given to water-soluble monomers, i.e., compounds whose solubility in water at 20° C. is at least 50 g/l. These include for example polyethylene glycol diacrylates and polyethylene glycol dimethacrylates, vinyl ethers of addition products of from 2 to 400 mol of ethylene oxide with 1 mol of a diol or polyol, ethylene glycol diacrylate, ethylene glycol dimethacrylate or triacrylates and trimethacrylates of addition products of from 6 to 20 mol of ethylene oxide with 1 mol of glycerol, pentaerythritol triallyl ether and divinylurea.

Useful monomers C further include compounds having at least one ethylenically unsaturated double bond and also at least one further functional group that is complementary in terms of its reactivity to carboxyl groups. Functional groups having complementary reactivity with regard to carboxyl groups include for example hydroxyl, amino, epoxy and aziridino groups. Compounds used include for example hydroxyalkyl esters of the aforementioned monoethylenically unsaturated carboxylic acids, such as 2-hydroxyethyl acrylate, 3-hydroxypropyl acrylate, 4-hydroxybutyl acrylate, 2-hydroxyethyl (meth)acrylate, 3-hydroxypropyl (meth)acrylate and 4-hydroxybutyl (meth)acrylate, allylpiperidinium bromide, N-vinylimidazoles, such as N-vinylimidazole, 1-vinyl-2-methylimidazole and N-vinylimidazolines, such as N-vinylimidazoline, 1-vinyl-2-methylimidazoline, 1-vinyl-2-ethylimidazoline or 1-vinyl-2-propylimidazoline, which are used in the form of the free bases, in quaternized form or as salt in the polymerization. It is also possible to use dimethylaminoethyl acrylate, dimethylaminoethyl methacrylate, diethylaminoethyl acrylate or diethylaminoethyl methacrylate. These basic esters are preferably used in quaternized form or as salt. Glycidyl (meth)acrylate is also useful.

Useful crosslinking monomers C further include compounds having at least two functional groups that are complementary in terms of their reactivity to the carboxyl group of the polymer. Useful functional groups are isocyanate, ester and amido groups as well as the aforementioned functional groups, such as hydroxyl, amino, epoxy and aziridine groups. Useful crosslinkers of this type include for example aminoalcohols, such as ethanolamine or triethanolamine, di- and polyols, such as 1,3-butanediol, 1,4-butanediol, ethylene glycol, diethylene glycol, triethylene glycol, tetraethylene glycol, polyethylene glycol, glycerol, polyglycerol, propylene glycol, polypropylene glycol, trimethylolpropane, pentaerythritol, polyvinyl alcohol, sorbitol, starch, block copolymers of ethylene oxide and propylene oxide, polyamines such as ethylenediamine, diethylenetriamine, triethylenetetramine, tetraethylenepentamine, pentaethylenehexamine and polyethyleneimines and also polyamines having molar masses of up to 4 000 000 in each case, esters such as sorbitan fatty acid esters, ethoxylated sorbitan fatty acid esters, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], diamides of carbonic acid, such as 1,6-hexamethylenediethyleneurea, diphenylmethanebis-4,4'-N,N'-diethyleneurea, haloepoxy compounds, such as epichlorohydrin and α-methylepifluorohydrin, polyisocyanates, such as 2,4-tolylene diisocyanate and hexamethylene diisocyanate, alkylene carbonates such as 1,3-dioxolan-2-one and 4-methyl-1,3-dioxolan-2-one, also bisoxazolines and oxazolidones, polyamidoamines and also their reaction products with epichlorohydrin, also polyquaternary amines, such as condensation products of dimethylamine with epichlorohydrin, homo- and copolymers of diallyldimethylammonium chloride and also homo- and copolymers of dimethylaminoethyl (meth)acrylate which have optionally been quaternized with, for example, methyl chloride.

The water absorbent polymers can be prepared by subjecting the monomers A, B and C to a free radical polymerization in aqueous solution, optionally in the presence of a suitable grafting base. The polymerization may be effected not only in homogeneous aqueous phase but also as a suspension polymerization, in which case the aqueous solution of the monomers forms the disperse phase.

Polymerization in aqueous solution is preferably conducted as gel polymerization. It involves for example 10–70% by weight aqueous solution of the monomers A, B and C being polymerized optionally in the presence of a suitable grafting base, by means of a polymerization initiator by utilizing the Trommsdorff-Norrish effect.

The polymerization is generally carried out in the temperature range from 0° C. to 150° C., preferably in the range from 10° C. to 100° C., and may be carried out not only at atmospheric pressure but also at superatmospheric or reduced pressure. As is customary, the polymerization may also be conducted in a protective gas atmosphere, preferably under nitrogen.

Industrial processes useful for preparing these products include all processes which are customarily used to make superabsorbents. Suitable measures are described for example in "Modern Superabsorbent Polymer Technology", F. L. Buchholz and A. T. Graham, Wiley-VCH, 1998, chapter 3, incorporated herein by reference. Useful polymerization reactors include the customary production reactors, especially belt reactors and kneaders in the case of solution polymerization (see "Modern Superabsorbent Polymer Technology", section 3.2.3). The polymers are particularly preferably produced by a continuous or batchwise kneading process.

Suitable initiators include in principle all compounds which decompose into free radicals on heating to the polymerization temperature. The polymerization may be initiated by the action of high energy radiation, for example UV radiation, in the presence of photoinitiators. Initiation of the polymerization by the action of electron beams on the polymerizable, aqueous mixture is also possible.

Suitable initiators include for example peroxo compounds such as organic peroxides, organic hydroperoxides, hydrogen peroxide, persulfates, perborates, azo compounds and redox catalysts. Water-soluble initiators are preferred. In some cases it is advantageous to use mixtures of different polymerization initiators, for example mixtures of hydrogen peroxide and sodium peroxodisulfate or potassium peroxodisulfate. Useful organic peroxides include for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl)

peroxodicarbonate, dicyclohexyl peroxodicarbonate, di(4-tert-butylcyclohexyl) peroxodicarbonate, dimyristyl peroxodicarbonate, diacetyl peroxodicarbonate, allyl peresters, cumene peroxyneodecanoate, tert-butyl per-3,5,5-trimethylhexanoate, acetyl cyclohexylsulfonyl peroxide, dilauryl peroxide, dibenzoyl peroxide and tert-amyl perneodecanoate. Particularly useful polymerization initiators include water-soluble azo initiators, e.g., 2,2'-azobis(2-amidinopropane) dihydrochloride, 2,2'-azobis(N,N'-dimethylene)isobutyramidine dihydrochloride, 2-(carbamoylazo)isobutyronitrile, 2,2'-azobis[2-(2'-imidazolin-2-yl)propane] dihydrochloride and 4,4'-azobis (4-cyanovaleric acid). The polymerization initiators mentioned are used in customary amounts, for example in amounts of from 0.01 to 5%, preferably from 0.05 to 2.0%, by weight, based on the monomers to be polymerized.

Redox initiators, which are preferred, are water-soluble initiators and include as the oxidizing component at least one of the above-specified peroxo compounds and as the reducing component for example ascorbic acid, glucose, sorbose, ammonium or alkali metal sulfite, bisulfite, thiosulfate, hyposulfite, pyrosulfite or sulfide, metal salts, such as iron(II) ions or sodium hydroxymethylsulfoxylate. The reducing component in the redox catalyst is preferably ascorbic acid or sodium sulfite. Based on the amount of monomers used in the polymerization, from $3\times10^{-6}$ to 1 mol % of the reducing component of the redox catalyst system and from 0.001 to 5.0 mol % of the oxidizing component of the redox catalyst is used, for example.

When the polymerization is initiated using high energy radiation, the initiator used is customarily a photoinitiator.

Polymers prepared by polymerization of the above-mentioned monoethylenically unsaturated acids with or without monoethylenically unsaturated comonomers and typically having a molecular weight of above 5000, preferably above 50 000, are postcrosslinked by reacting them with compounds having at least two groups that are reactive toward acid groups. This reaction may take place at room temperature or else at elevated temperatures of up to 220° C. The crosslinkers used are the aforementioned monomers C, which have at least two functional groups having complementary reactivity with regard to carboxyl groups.

The crosslinkers for postcrosslinking or gel crosslinking are added to the resultant polymers in amounts of from 0.5 to 20% by weight, preferably from 1 to 14% by weight, based on the amount of the polymer.

The polymers of the invention are generally obtained after polymerization as hydrogels having a moisture content of for example from 0 to 90%, usually from 20 to 90 by weight, which are generally initially coarsely comminuted by known methods. Coarse comminution of the hydrogels is effected by means of customary tearing and/or cutting tools, for example by the action of a discharge pump in the case of polymerization in a cylindrical reactor or by a cutting roll or cutting roll combination in the case of belt polymerization.

When the A monomers have not been used in neutralized form, the acidic polymer obtained can be adjusted to the desired degree of neutralization of generally at least 25 mol %, preferably at least 50 mol %, preferably from 50 to 100 mol %, based on acid-functional monomer units. Alternatively, the degree of neutralization may also be adjusted before or during the polymerization, for example in a kneader.

Useful neutralizing agents include alkali metal bases or ammonia/amines. Preference is given to the use of aqueous sodium hydroxide solution or aqueous potassium hydroxide solution. However, neutralization may also be effected using sodium carbonate, sodium bicarbonate, potassium carbonate or potassium bicarbonate or other carbonates or bicarbonates or ammonia. Moreover, primary, secondary and tertiary amines may be used for neutralization.

The thus obtained, preferably (partially) neutralized polymer is subsequently dried at elevated temperature, for example in the range from 80° C. to 250° C., especially in the range from 100° C. to 180° C., by known processes (see "Modern Superabsorbent Polymer Technology" section 3.2.5). This provides the polymers in the form of powders or granules which, if appropriate, are additionally subjected to several grinding and classifying operations to set the particle size (see "Modern Superabsorbent Polymer Technology" sections 3.2.6 and 3.2.7).

Preferably, the particulate polymers obtained are then surface postcrosslinked. To effect surface postcrosslinking, compounds capable of reacting with the acid functional groups are applied to the surface of the polymer particles, preferably in the form of an aqueous solution. The aqueous solution may contain water-miscible organic solvents. Suitable solvents are alcohols such as methanol, ethanol, i-propanol or acetone.

Suitable postcrosslinkers include for example:
- di- or polyglycidyl compounds such as diglycidyl phosphonates or ethylene glycol diglycidyl ether, bischlorohydrin ethers of polyalkylene glycols,
- alkoxysilyl compounds,
- polyaziridines, aziridine compounds based on polyethers or substituted hydrocarbons, for example bis-N-aziridinomethane,
- polyamines or polyamidoamines and also their reaction products with epichlorohydrin,
- polyols such as ethylene glycol, 1,2-propanediol, 1,4-butanediol, glycerol, methyltriglycol, polyethylene glycols having an average molecular weight $M_w$ of 200–10 000, di- and polyglycerol, pentaerythritol, sorbitol, the ethoxylates of these polyols and their esters with carboxylic acids or carbonic acid such as ethylene carbonate or propylene carbonate,
- carbonic acid derivatives such as urea, thiourea, guanidine, dicyandiamide, 2-oxazolidinone and its derivatives, bisoxazoline, polyoxazolines, di- and polyisocyanates,
- di- and poly-N-methylol compounds such as, for example, methylenebis(N-methylolmethacrylamide) or melamine-formaldehyde resins,
- compounds having two or more blocked isocyanate groups such as, for example, trimethylhexamethylene diisocyanate blocked with 2,2,3,6-tetramethylpiperidin-4-one.

If necessary, acidic catalysts may be added, for example p-toluenesulfonic acid, phosphoric acid, boric acid or ammonium dihydrogenphosphate.

Particularly suitable postcrosslinkers are di- or polyglycidyl compounds such as ethylene glycol diglycidyl ether, the reaction products of polyamidoamines with epichlorohydrin and 2-oxazolidinone.

The crosslinker solution is preferably applied by spraying with a solution of the crosslinker in conventional reaction mixers or mixing and drying equipment such as Patterson-Kelly mixers, DRAIS turbulence mixers, Lödige mixers, screw mixers, plate mixers, fluidized bed mixers and Schugi-Mix. The spraying of the crosslinker solution may be followed by a heat treatment step, preferably in a downstream dryer, at from 80 to 230° C., preferably at from 80 to 190° C., particularly preferably at from 100 to 160° C., for from 5 minutes to 6 hours, preferably from 10 minutes to 2 hours, particularly preferably from 10 minutes to 1 hour, during which not only cracking products but also solvent fractions can be removed. But the drying may also take place in the mixer itself, by heating the jacket or by blowing in a preheated carrier gas.

The water absorbent of the invention is prepared by starting with a particulate water absorbent polymer, which is present in dried form or as a comminuted hydrogel having the above-specified moisture content, and applying a water insoluble metal phosphate to the surface of the particles.

For this, the particulate water absorbent polymer can be intimately mixed for example with a finely divided water insoluble metal phosphate. The finely divided water-insoluble metal phosphate is usually added at room temperature to the particulate water absorbent polymer and mixed in until a homogeneous mixture is present. Mixing can be effected using customary apparatus, for example a tumble mixer, a belt screw mixer or a silo screw mixer. The mixing with the finely divided water insoluble metal phosphate may take place before or after any surface postcrosslinking, for example during the heat aftertreatment step following the application of the postcrosslinking agent.

The finely divided water insoluble metal phosphate preferably has a median particle size of less than 400 μm, especially of less than 100 μm, more preferably less than 50 μm, particularly preferably less than 10 μm and most preferably in the range from 2 to 7 μm.

Alternatively, a slurry of a finely divided water insoluble metal phosphate can be applied to a particulate water absorbent polymer. The particle size of the water insoluble metal phosphate is preferably as specified above. The slurry is applied for example by spraying. Useful dispersion media for preparing the slurry include water, organic solvents, such as alcohols, for example methanol, ethanol, isopropanol, ketones, for example acetone, methyl ethyl ketone or mixtures of water with the aforementioned organic solvents. The slurry can be applied in conventional reaction mixers or mixing and drying systems as described above at a temperature in the range from room temperature to less than the boiling point of the dispersion medium, preferably about room temperature. It is appropriate to combine the application of the slurry with a surface postcrosslinking step by dispersing the finely divided water insoluble metal phosphate in the solution of the postcrosslinking agent. Alternatively, the slurry can also be applied before or after the surface postcrosslinking step. The application of the slurry may be followed by a drying step.

In a further embodiment of the invention, the water insoluble metal phosphate is generated in situ on the surface of the water absorbent polymer by contacting a first aqueous solution containing phosphate ions with a second aqueous solution in the presence of a particulate water absorbent polymer, the second solution containing a water soluble salt of a metal forming a water insoluble phosphate. The counterions for the solution containing phosphate ions are preferably alkali metal ions, such as sodium or potassium ions. The first solution can alternatively be diluted phosphoric acid. The second solution contains ions of at least one metal ion which forms a water insoluble phosphate, such as calcium, magnesium, strontium, barium, zinc, iron, aluminum, titanium, zirconium, hafnium, tin, cerium, scandium, yttrium or lanthanum or mixtures thereof, preferably calcium. It is present as a solution of a sufficiently water soluble salt, for example a halide, such as chloride, bromide, iodide, hydroxide, sulfate or nitrate. The desired water insoluble metal phosphate precipitates on contact of the first aqueous solution with the second aqueous solution as a result of its solubility product being exceeded. In a particularly preferred embodiment, a solution of calcium chloride is used as the first aqueous solution and a solution of primary, secondary or tertiary sodium phosphate as the second aqueous solution. Tertiary calcium phosphate is formed in situ, and it slowly converts into hydroxyl apatite. The in situ precipitation of the water insoluble metal phosphate on the surface of the water absorbent polymer can take place before, during or after the surface aftertreatment. If desired, a drying step is carried out next.

The water absorbents of the invention are very useful as absorbents for water and aqueous fluids, especially body fluids. They can beneficially be used for producing hygiene articles such as diapers, incontinence pads and briefs, tampons or sanitary napkins. They can further be used for soil improvement, for example as a water retainer in market gardening.

The examples hereinbelow illustrate the invention.

I Description of the Test Methods

1. Centrifuge Retention Capacity (CRC: Centrifuge Retention Capacity)

This method measures the free swellability of the hydrogel-forming polymer in a teabag. 0.2000±0.0050 g of dried polymer (particle size fraction 106–850 μm) is sealed into a teabag 60×85 mm in size. The teabag is then soaked for 30 minutes in 0.9% by weight saline solution (at least 0.83 l of saline/1 g of polymer powder). The teabag is then centrifuged for 3 minutes at 250 G. The amount of liquid absorbed is determined by weighing the centrifuged teabag.

2. Absorbency Under Load (AUL) (0.7 psi)

The measuring cell for determining AUL 0.7 psi is a Plexiglas cylinder 60 mm in internal diameter and 50 mm in height. Adhesively attached to its underside is a stainless steel mesh floor having a mesh size of 36 μm. The measuring cell further includes a plastic plate having a diameter of 59 mm and a weight which can be placed in the measuring cell together with the plastic plate. The weight of the plastic plate and the weight totals 1345 g. AUL 0.7 psi is determined by measuring the weight of the empty Plexiglas cylinder and of the plastic plate and recorded as $W_0$. 0.900±0.005 g of hydrogel-forming polymer (particle size distribution 106–800 μm) is then weighed into the Plexiglas cylinder and distributed very uniformly over the stainless steel mesh floor. The plastic plate is then carefully placed in the Plexiglas cylinder, the entire unit is weighed and the weight is recorded as $W_a$. The weight is then placed on the plastic plate in the Plexiglas cylinder. A ceramic filter plate 120 mm in diameter and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglas cylinder containing hydrogel-forming polymer is then placed with plastic plate and weight on top of the filter paper and left there for 60 minutes. At the end of this period, the complete unit is removed from the filter paper and Petri dish and subsequently the weight is removed from the Plexiglas cylinder. The Plexiglas cylinder containing swollen hydrogel is weighed together with the plastic plate and the weight recorded as $W_b$.

AUL is calculated by the following equation:

$$AUL\ 0.7\ psi[g/g]=[W_b-W_a]/[W_a-W_0]$$

3. Saline Flow Conductivity (SFC)

The test method for determining SFC is described in U.S. Pat. No. 5,599,335.

4. Swell Rate (SR)

This method determines the initial swellability of a hydrogel in the absence of a confining pressure. To determine the swell rate, 3.000±0.005 g of the dried hydrogel to be tested (moisture content <5% by weight) are weighed into an 18/10 stainless steel ointment tub 200 mm in diameter and 100 mm in height and homogeneously distributed into the center of the semicircle bottom. A dispenser is then used to add 60.0 g of 0.9% by weight sodium chloride solution exactly into the center. The time t is taken in seconds (stop watch with ¹⁄₁₀ seconds scale) which passes between the addition of the sodium chloride solution and the adsorption of the last drop of liquid via the hydrogel. It is customary to report the average of a double determination.

The swell rate (SR) is calculated as follows:

$$SR\ [g/g \cdot s] = \frac{\text{Amount of adsorbed saline solution}}{\text{Amount of dry hydrogel} \cdot \text{adsorption time}}$$

The swell rate accordingly indicates how many g of saline solution are absorbed per hydrogel per second.

II PREPARATION EXAMPLES

Example 1

A glass bottle having a capacity of at least 2.5 l was charged with 1 kg of commercially available hydrogel of the type HySorb® M7910 (BASF AG, crosslinked sodium polyacrylate), followed by 0.5% by weight of commercially available hydroxyl apatite (sold by Budenheim), and the contents were initially coarsely premixed. The hydroxyl apatite used had an average particle size of 3 μm and 5 μm. The bottle was then rolled on a roll mill for about 30 min. Thereafter, the mixture was homogeneous. The test results of the water absorbents obtained in this way are reported in table 1.

TABLE 1

| Run | Average particle size [μm] | CRC [g/g] | AUL 0.7 psi [g/g] | SR [g/g · s] | SFC × $10^{-7}$ [cm³ · s/g] |
|---|---|---|---|---|---|
| A (comparison) | — | 28.0 | 23.0 | 0.14 | 41 |
| B + 0.5% of calcium phosphate | 5 | 29.0 | 23.6 | 0.20 | 58 |
| C + 0.5% of calcium phosphate | 3 | 29.9 | 24.4 | 0.25 | 70 |

Example 2

Example 1 was repeated except that the HySorb® M7910 hydrogel was replaced by the same amount of the commercially available hydrogel of the type HySorb® M7900 (crosslinked sodium polyacrylate). The test results of the water absorbents thus obtained are reported in table 2.

TABLE 2

| Run | Average particle size [μm] | CRC [g/g] | AUL 0.7 psi [g/g] | SR [g/g · s] | SFC × $10^{-7}$ [cm³ · s/g] |
|---|---|---|---|---|---|
| D (comparison) | — | 24.0 | 20.7 | 0.13 | 62 |
| E + 0.5% of calcium phosphate | 5 | 24.7 | 21.0 | 0.12 | 133 |

Example 3

Example 1 was repeated except that different amounts of calcium triphosphate having an average particle size of 5 μm were used. The test results of the water absorbents thus obtained are reported in table 3.

TABLE 3

| Run | CRC [g/g] | AUL 0.7 psi [g/g] | SFC × $10^{-7}$ [cm³ · s/g] |
|---|---|---|---|
| F (comparison) | 27.9 | 23.1 | 45 |
| G + 0.1% of calcium phosphate | 30.0 | 24.6 | 54 |
| H + 0.2% of calcium phosphate | 30.2 | 24.7 | 57 |
| I + 0.4% of calcium phosphate | 29.0 | 24.1 | 68 |
| J + 0.8% of calcium phosphate | 29.3 | 24.2 | 78 |

It is evident that the surface treatment of the water absorbent polymer with a finely divided calcium triphosphate leads to increased centrifuge retention capacity, absorbency under load and saline flow conductivity.

Example 4

The examples which follow illustrate the application of the water-insoluble metal phosphate from a suspension. The results are reported in table 4.

Example 4.1 (Comparative)

1 500 g of a commercially available superabsorbent of the type ASAP 403 (BASF Corp., Aberdeen) were initially charged to a Lödige laboratory mixer and sprayed with 75 g of isopropanol by means of a two-material nozzle. The polymer obtained was thereafter dried in a drying cabinet.

Example 4.2

1 500 g of a commercially available superabsorbent of the type ASAP 403 were initially charged to a Lödige laboratory mixer and sprayed with 4.5 g of tricalcium phosphate (C 13-09, SF, microfine powder, food grade—obtained from Chemische Fabrik Budenheim), which had been suspended in 75 g of isopropanol by stirring, by means of a two-material nozzle. The polymer obtained was thereafter dried in a drying cabinet.

Example 4.3

1 500 g of a commercially available superabsorbent of the type ASAP 403 were initially charged to a Lödige laboratory mixer and sprayed with 4.5 g of tricalcium phosphate (C 13-09, SF), which had been suspended in 30 g of water by stirring, by means of a two-material nozzle. The powder obtained was thereafter dried in a drying cabinet.

Example 4.4 (Comparative)

1 500 g of a commercially available superabsorbent of the type ASAP 403 were initially charged to a Lödige laboratory mixer and sprayed with 4.5 g of aerosol of the type Sipernat 22 S (from Degussa), which had been suspended in 75 g of isopropanol by stirring, by means of a two-material nozzle. The polymer obtained was thereafter dried in a drying cabinet.

Example 4.5 (Comparative)

1 500 g of a commercially available superabsorbent of the type ASAP 403 were initially charged to a Lödige laboratory mixer and sprayed with 4.5 g of aerosol of the type Sipernat D 17 (from Degussa), which had been suspended in 75 g of isopropanol by stirring, by means of a two-material nozzle. The polymer obtained was thereafter dried in a drying cabinet.

Example 4.6 (Comparative)

1 500 g of a commercially available superabsorbent of the type ASAP 500 (BASF Corp.) were initially charged to a Lödige laboratory mixer and sprayed with 60 g of isopropanol by means of a two-material nozzle. The polymer obtained was not dried. This is the comparative sample to example 4.7.

Example 4.7

1 500 g of a commercially available superabsorbent of the type ASAP 403 were initially charged to a Lödige laboratory mixer and sprayed with 2.25 g of tricalcium phosphate (C 13-09, SF), which had been suspended in 60 g of isopropanol by stirring, by means of a two-material nozzle. The polymer obtained was not dried.

TABLE 4

| Example No. | CRC [g/g] | AUL 0.7 psi [g/g] | SFC × $10^{-7}$ [$cm^3 \cdot s/g$] | QG [$g/g \cdot s$] |
| --- | --- | --- | --- | --- |
| 4.1* | 28.7 | 24.3 | 56 | 0.18 |
| 4.2 | 28.8 | 24.2 | 89 | 0.21 |
| 4.3 | 28.1 | 24.0 | 80 | 0.20 |
| 4.4* | 28.7 | 21.5 | 70 | 0.21 |
| 4.5* | 28.6 | 21.6 | 74 | 0.12 |
| 4.6* | 29.2 | 22.6 | 23 | — |
| 4.7 | 29.5 | 22.9 | 31 | — |

*comparative examples

Example 5

The examples which follow illustrate the application of the water-insoluble metal phosphate in the course of surface postcrosslinking. The results are reported in table 5 (the SFC was calculated as the average of 5 measurements).

HYDROGEL PREPARATION EXAMPLE

In a 40 l plastic bucket, 6.9 kg of glacial acrylic acid were 75 mol % neutralized by stirring into dilute aqueous sodium hydroxide solution and cooling by means of a heat exchanger and diluted with water to 30 kg of reaction material. This solution was admixed with 50 g of polyethylene glycol 400 diacrylate crosslinker by stirring and the sealed bucket was inertized by passing nitrogen through it. The polymerization was then started by adding 400 mg of hydrogen peroxide and 200 mg of ascorbic acid and 10 g of sodium persulfate. After the reaction had ended, the gel was mechanically comminuted. The comminuted gel was then dried in a laboratory drying cabinet at 150° C. for 3 h, ground using a laboratory roll mill and finally sieved off at from 200 to 850 μm. This was the base polymer used in the examples which follow.

Example 5.1 (Comparative)

1 200 g of the base polymer in a Lödige plowshare laboratory mixer were sprayed with postcrosslinker solution of the following composition: 1.5% by weight of isopropanol, 3.5% by weight of water, 0.12% by weight of 2-oxazolidinone, each percentage being based on polymer used, by means of a two-material nozzle. The moist product was subsequently heat treated at 175° C. for 60 min in a circulating air drying cabinet. The dried product was subsequently sieved off at 850 μm to remove clumps.

Example 5.2

1 200 g of the base polymer in a Lödige plowshare laboratory mixer were sprayed with crosslinker solution of the following composition: 1.5% by weight of isopropanol, 3.5% by weight of water, 0.12% by weight of 2-oxazolidinone, 0.2% by weight of tricalcium phosphate (C 13-09, SF), each percentage being based on polymer used. The moist polymer was then heat treated at 175° C. for 60 min in a circulating air drying cabinet. The dried product was subsequently sieved off at 850 μm to remove clumps.

Example 5.3

1 200 g of the base polymer in a Lödige plowshare laboratory mixer were sprayed with crosslinker solution of the following composition: 1.5% by weight of isopropanol, 3.5% by weight of water, 0.10% by weight of ethylene glycol diglycidyl ether, 0.2% by weight of tricalcium phosphate (C 13-09, SF), each percentage being based on polymer used. The moist polymer was then heat treated at 150° C. for 60 min in a circulating air drying cabinet. The dried product was subsequently sieved off at 850 μm to remove clumps.

Example 5.4

1 200 g of the base polymer were initially mixed with 0.30% by weight of pulverulent tricalcium phosphate (C 13-09, SF) in a Waring plowshare laboratory mixer for 30 min; this was followed by spraying with crosslinker solution of the following composition: 1.5% by weight of isopropanol, 3.5% by weight of water, 0.10% by weight of ethylene glycol diglycidyl ether, each percentage being based on polymer used. The moist product was subsequently heat treated at 150° C. for 60 min in a circulating air drying cabinet. The dried product was subsequently sieved off at 850 μm to remove clumps.

TABLE 5

| Example No. | CRC [g/g] | AUL 0.7 psi [g/g] | SFC × $10^{-7}$ [$cm^3 \cdot s/g$] |
| --- | --- | --- | --- |
| 5.1* | 31.0 | 24.5 | 18 |
| 5.2 | 30.9 | 24.7 | 32 |
| 5.3 | 31.7 | 24.9 | 34 |
| 5.4 | 31.5 | 25.0 | 29 |

*comparative example

We claim:

1. A water absorbent comprising particles of a water absorbent polymer whose surface is virtually exclusively associated with a water insoluble metal phosphate with a median particle size of 2 to 400 μm, wherein the water insoluble metal phosphate is present in an amount of 0.01 to 5% by weight based on the weight of the water absorbent polymer.

2. The water absorbent of claim 1 wherein the water insoluble metal phosphate is a phosphate of formula $M_4P_2O_7$, $M_2HPO_4$ or $M_3PO_4$, wherein M is one equivalent of a metal selected from the group consisting of calcium, magnesium, strontium, barium, zinc, iron, aluminum, titanium, zirconium, hafnium, tin, cerium, scandium, yttrium, lanthanum and mixtures thereof.

3. The water absorbent of claim 2 wherein the water insoluble metal phosphate is selected from the group consisting of calcium hydrogen phosphate, tertiary calcium phosphate, apatite, rhenania phosphate, Thomas flour, berlinite, and mixtures thereof.

4. The water absorbent of claim 1 wherein said water absorbent polymer is polymerized from:
   49.9 to 99.9% by weight of at least one monomer A selected from the group consisting of mono-ethylenically unsaturated acids and salts thereof,
   0 to 50% by weight of at least one mono-ethylenically unsaturated monomer B other than said monomer A, and
   0.001 to 20% by weight of at least one crosslinking monomer C.

5. The water absorbent of claim 1 wherein said water absorbent polymer is surface post-crosslinked.

6. A process for producing a water absorbent of claim 1 which comprises
   a) spraying a slurry of a finely divided water insoluble metal phosphate to a particulate water absorbent polymer; or
   b) contacting a first aqueous solution con-taining phosphate ions with a second aqueous solution in the presence of a particulate water absorbent poly-mer, said second solution containing a water soluble salt of a metal forming a water insoluble phosphate.

7. The process of claim 6 wherein said particulate water absorbent polymer is surface post-crosslinked concurrently with said step a), b), or thereafter.

8. The process of claim 6 wherein said particulate water absorbent polymer is in the form of a comminuted hydrogel having a moisture content of from 0% by weight to 90% by weight.

9. A method of absorbing body fluids comprising the step of contacting a body fluid with water absorbent particles of claim 1.

10. A hygiene article comprising water absorbent particles of claim 1.

11. A method of improving the condition of a soil comprising contacting said soil with water absorbent particles of claim 1.

12. The water absorbent of claim 1 wherein the water absorbent is obtained by a process which comprises
   a) spraying a slurry of finely divided water insoluble metal phosphate to a particulate water absorbent polymer or
   b) contacting a first aqueous solution containing phosphate ions with a second aqueous solution in the presence of a particulate water absorbent polymer, said second solution containing a water soluble salt of a metal forming a water insoluble phosphate.

13. The water absorbent of claim 1 wherein the fraction of said water insoluble metal phosphate is in the range from 0.05 to 2.5% by weight, based on the weight of said water absorbent polymer.

14. A water absorbent comprising particles of a water absorbent polymer whose surface is virtually exclusively associated with a water insoluble metal phosphate with a median particle size of 2 to 400 μm, wherein the water insoluble metal phosphate is present in an amount of 0.01 to 5% by weight based on the weight of the water absorbent polymer, said water absorbent being obtained by a process which comprises
   a) spraying a slurry of a finely divided water insoluble metal phosphate to a particulate water absorbent polymer or
   b) contacting a first aqueous solution containing phosphate ions with a second aqueous solution in the presence of a particulate water absorbent polymer, said second solution containing a water soluble salt of a metal forming a water insoluble phosphate.

15. The water absorbent of claim 14 wherein the water insoluble metal phosphate is a phosphate of the formula $M_4P_2O_7$, $M_2HPO_4$ or $M_3PO_4$, wherein M is one equivalent of a metal selected from the group consisting of calcium, magnesium, strontium, barium, zinc, iron, aluminum, titanium, zirconium, hafnium, tin, cerium, scandium, yttrium, lanthanum and mixtures thereof.

16. The water absorbent of claim 15 wherein the water insoluble metal phosphate is selected from the group consisting of calcium hydrogen phosphate, tertiary calcium phosphate, apatite, rhenania phosphate, Thomas flour, berlinite and mixtures thereof.

17. The water absorbent of claim 14 wherein said water absorbent polymer is polymerized from:
   49.9 to 99.9% by weight of at least one monomer A selected from the group consisting of monoethylenically unsaturated acids and salts thereof,
   0 to 50% by weight of at least one monoethylenically unsaturated monomer B other than said monomer A, and
   0.001 to 20% by weight of at least one crosslinking monomer C.

18. The water absorbent of claim 14 wherein said water absorbent polymer is surface post-crosslinked.

19. The water absorbent of claim 14 wherein the fraction of said water insoluble metal phosphate is in the range from 0.05 to 2.5% by weight, based on the weight of said water absorbent polymer.

20. A process for producing a water absorbent of claim 14 which comprises
   b) spraying a slurry of a finely divided water insoluble metal phosphate to a particulate water absorbent polymer; or
   c) contacting a first aqueous solution containing phosphate ions with a second aqueous solution in the presence of a particulate water absorbent polymer, said second solution containing a water soluble salt of a metal forming a water insoluble phosphate.

21. The process of claim 20 wherein said particulate water absorbent polymer is surface post-crosslinked concurrently with said step b) or c), or thereafter.

22. The process of claim 20 wherein said particulate water absorbent polymer is in the form of a comminuted hydrogel having a moisture content of from 0% by weight to 90% by weight.

23. A method of absorbing body fluids comprising the step of contacting a body fluid with water absorbent particles of claim 14.

24. A hygiene article comprising water absorbent particles of claim 14.

25. A method of improving the condition of a soil comprising contacting said soil with water absorbent particles of claim 14.

* * * * *

UNITED STATES PATENT AND TRADEMARK OFFICE
CERTIFICATE OF CORRECTION

PATENT NO. : 6,831,122 B2
DATED : December 14, 2005
INVENTOR(S) : Daniel et al.

It is certified that error appears in the above-identified patent and that said Letters Patent is hereby corrected as shown below:

Column 15,
Line 22, "mono-ethylenically" should be -- monoethylenically --
Line 34, "con-taining" should be -- containing --
Line 36, "poly-mer" should be -- polymer --

Signed and Sealed this

Seventeenth Day of May, 2005

JON W. DUDAS
*Director of the United States Patent and Trademark Office*